United States Patent [19]

Banno et al.

[11] 4,265,544
[45] May 5, 1981

[54] LIQUID AGITATION APPARATUS FOR AN ABSORBANCE MEASURING APPARATUS

[75] Inventors: Taiichi Banno; Hideaki Ida, both of Hachioji, Japan

[73] Assignee: Olympus Optical Co., Ltd., Japan

[21] Appl. No.: 16,959

[22] Filed: Mar. 5, 1979

[30] Foreign Application Priority Data

May 24, 1978 [JP] Japan .............................. 53/70911[U]

[51] Int. Cl.³ ...................... G01N 21/00; G01N 21/75
[52] U.S. Cl. .................................... 356/427; 356/244; 366/127; 422/68; 422/99; 435/291; 435/808
[58] Field of Search ............................ 422/68, 99, 73; 435/291, 808; 366/127, 110, 112, 116; 356/409, 414, 440, 244, 427

[56] References Cited

U.S. PATENT DOCUMENTS

| 3,217,877 | 11/1965 | Honjyo et al. | 356/427 X |
| 3,322,956 | 5/1967 | Shah | 435/808 X |
| 3,464,674 | 9/1969 | Pick | 366/112 |
| 3,627,423 | 12/1971 | Knapp et al. | 356/427 X |
| 3,847,482 | 11/1974 | Sokol et al. | 356/244 X |

FOREIGN PATENT DOCUMENTS 2820441 11/1978 Fed. Rep. of Germany ...... 435/808 X

Primary Examiner—Arnold Turk
Attorney, Agent, or Firm—Ostrolenk, Faber, Gerb & Soffen

[57] ABSTRACT

A liquid agitation apparatus comprises a transparent reaction vessel for containing a reaction solution to be examined, a holder for holding the reaction vessel, and a rotary solenoid for imparting a mechanical vibration to the holder. The mechanical vibration from the rotary solenoid is effective to agitate the reaction solution automatically.

5 Claims, 2 Drawing Figures

LIQUID AGITATION APPARATUS FOR AN ABSORBANCE MEASURING APPARATUS

BACKGROUND OF THE INVENTION

The invention relates to a liquid agitation apparatus, and more particularly, to such apparatus which is intended to be used in an automatic agitation of a reaction solution comprising a mixture of a liquid to be examined and a reagent.

To determine the quantity of a substance such as an enzyme contained in a blood sample by means of a chemical analyzer, a coenzyme is mixed with the liquid sample and the absorbance of the coenzyme determined. With this determining technique, there exists a proportional relationship between the absorbance and the time, a change in the absorbance indicating the quantity of the enzyme. It is known that the quantity of the enzyme is a function of temperature. Consequently, in order to assure reliable data, it is essential that the liquid to be examined, such as blood, be uniformly mixed with the reagent and that the mixed reaction solution be maintained at a constant temperature during the determination process.

A conventional apparatus used to make such a determination will be described with reference to FIG. 1. A thermostat block 1 is kept at a constant temperature in an automatic manner by using the combination of a heating element and a temperature sensor. It includes a preheater assembly 1a and a measuring cell 1b. The preheater assembly 1a is formed with a plurality of openings 3 which receive removable reaction vessels 2 in the form of transparent, hollow square pillars which contain a reaction solution. The measuring cell 1b includes an opening 4 which is adapted to receive a reaction vessel 2 containing the reaction solution, and an opening 5 which is formed to extend through the opening 4 for the purpose of obtaining photometric data. A light source 6, which may comprise a tungsten lamp, emits a photometric flux of radiation passing substantially through the center of one side 2a of the vessel 2 which is exposed through the opening 5. A photoelectric transducer element 7, which may comprise a silicon blue cell, is disposed on the opposite side of the cell from the lamp to receive light passing through the cell.

In using the conventional apparatus illustrated in FIG. 1, a plurality of reaction vessels 2 containing a reagent are loaded in the openings 3 for the purpose of preheating. When a given temperature is reached, one of the vessels 2 is removed, a specimen is added thereto and is shaken by hand or by using a stirring rod, and the vessel 2 is loaded in the opening 4. A flux of radiation P having a given optical wavelength is emitted by the source 6, passes through the opening 5 and through the reaction solution contained in the vessel 2 disposed in the opening 4, and finally received by the transducer element 7. The element 7 produces an electrical signal in accordance with the magnitude of the transmitted portion of the radiation flux P and applies the signal to an arithmetic circuit, which calculates the absorbance of the reaction solution.

In the arrangement described above, the apparatus is not provided with stirring means in itself and hence the vessel 2 must be shaken by hand or stirred by some other means after it is removed from opening 3. This represents both an operational inconvenience and a cause of error in the measurement in that the vessel 2 is removed from the apparatus and a stirring rod, which may be at a different temperature, is brought into contact with the reaction solution, thus causing a rapid drop in the temperature of the preheated solution. Also, the period of agitation varies from vessel to vessel, so that the agitation of the solution may be insufficient.

SUMMARY OF THE INVENTION

It is an object of the invention to provide a liquid agitation apparatus in which a reaction vessel is carried by a holder which is subject to a mechanical vibration for automatically agitating a reaction solution contained therein, thus avoiding a change in the temperature of the reaction solution in response to extraneous factors.

It is another object of the invention to provide a liquid agitation apparatus of the kind described in which a mechanical vibration is produced by a rotary solenoid to enable the establishment of a desired agitation period which may be either varied or maintained constant.

In accordance with the invention, the agitation apparatus comprises a holder which carries a reaction vessel containing a reaction solution, and means for applying a mechanical vibration to the holder. In this manner, the agitation takes place automatically. The means for applying a mechanical vibration may comprise a rotary solenoid, which may be controlled by a control circuit such as an electronic timer to choose a desired agitation period.

With the present invention, it becomes unnecessary to remove a reaction vessel from the apparatus or to shake it by hand or to use a stirring rod for the purpose of agitation, and it is thus possible to eliminate a change in the temperature of the reaction solution which may cause an error in the data. Because the agitation period can be chosen as desired, an optimum agitation period may be chosen depending on the ratio of the quantity of the liquid to be examined to that of reagent. Similarly, a uniform agitation period can be maintained for several reaction vessels. Finally, the time required for complete agitation is minimized.

DESCRIPTION OF PREFERRED EMBODIMENT

Figure 1:
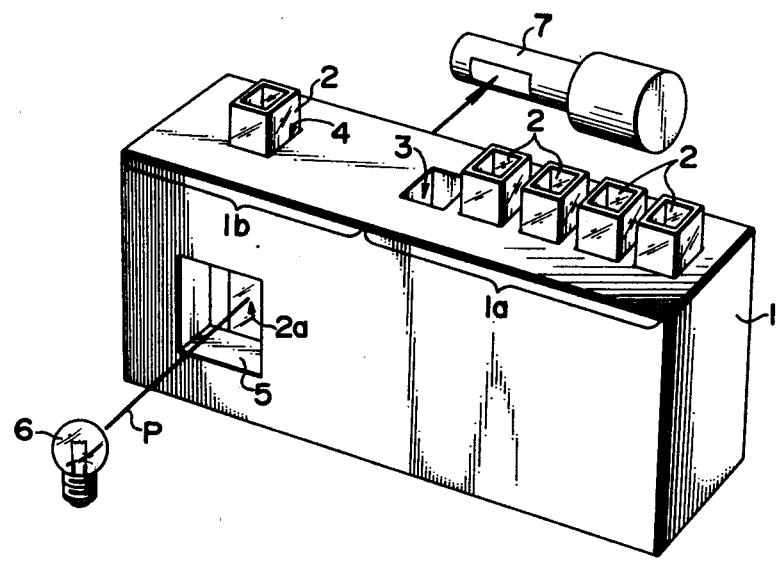
FIG. 1 is a perspective view of a conventional absorbance measuring apparatus.
Figure 2:
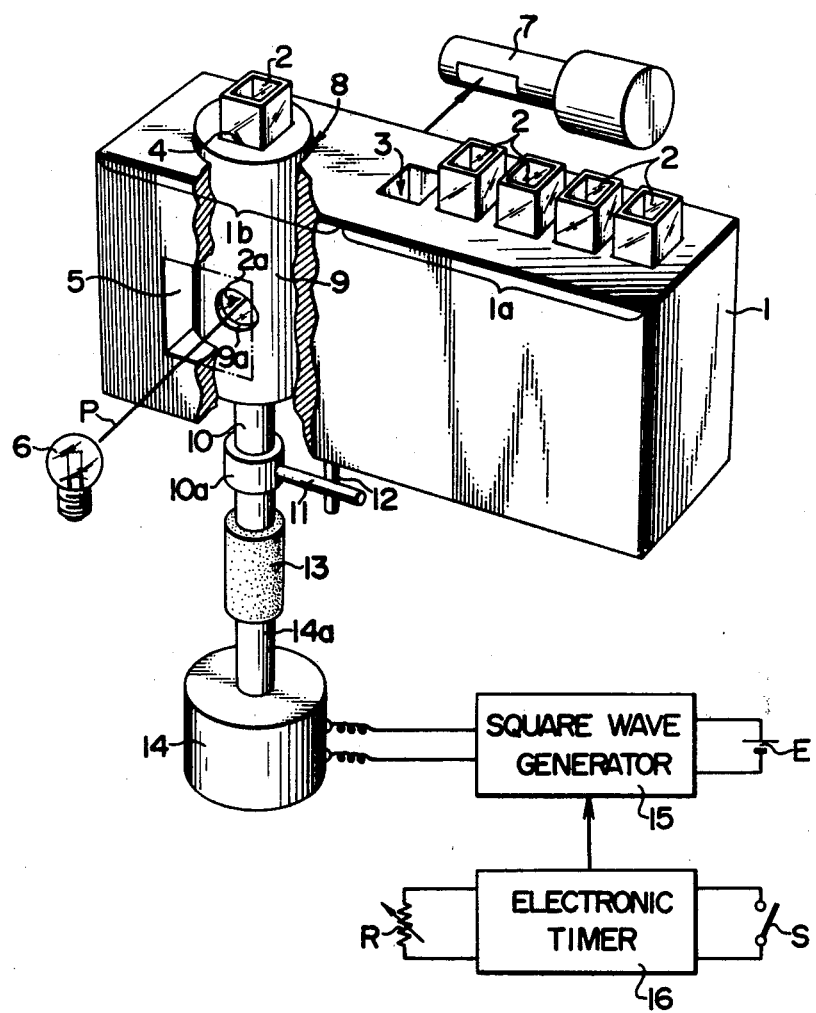
FIG. 2 is a perspective view of a liquid agitation apparatus according to one embodiment of the invention.

Referring to FIG. 2, there is shown a liquid agitation apparatus according to the invention. The apparatus includes a thermostat block 1 including a measuring cell 1b in which a circular through opening 8 is formed. A cylindrical holder 9 is fitted in the opening 8 in a rotatable and vertically slidable manner and in good thermal contact therewith, and is centrally formed with an axially extending, square opening 4 in which a reaction vessel 2 may be removably received. To permit the taking of photometric data, two opposing openings 9a are formed in opposite sides of the holder 9, and communicate with the opening 4. A support shaft 10 is integrally connected with the central portion of the bottom surface of the holder 9, and has a positioning member 11 mounted thereon by means of a mounting ring 10a intermediate its length. The positioning member 11 is adapted to engage a lug 12 which is secured to the block 1 so that when the positioning member 11 abuts the lug 12, the openings 9a formed in the holder 9 are aligned with a photometric opening 5 formed in the block 1 and also with the optical axis of radiation flux P which is emitted by a lamp 6.

The lower end of the shaft 10 is connected with the output shaft 14a of a rotary solenoid 14, by means of a joint 13 which comprises a coiled spring or rubber tube with circumferential torsional resilience. The shafts 10, 14a are so connected that the positioning member 11 abuts the lug 12 in the unenergized position of the solenoid 14 as the shaft 10 is subject to the elastical circumferential restoring force of the joint 13.

The rotary solenoid 14 is connected with a square wave generator 15, which is fed by a power source E, and to which an electronic timer 16 is connected. The timer 16 responds to the closure of a start switch S by activating the oscillator 15 for a time interval which depends on the resistance of a variable resistor R. It may include a CR timer.

In operation, a reagent is added to one of the reaction vessels 4 which contain a liquid to be examined and which are preheated within the openings 3 of the preheater assembly 1a. The particular one vessel is loaded into the opening 4 formed within the holder 9. When the start switch S is closed, the oscillator 15 feeds a square wave signal to the solenoid 14 for a time interval which is preselected by the adjustment of the variable resistor R. In response to the square wave signal, the output shaft 14a rotates in a reciprocatory manner while undergoing a slight vertical movement. The reciprocatory rotation is transmitted through the joint 13 to the shaft 10, so that the holder 9 also rotates in a reciprocatory manner while undergoing a slight vertical movement within the opening 8 formed in the thermostat block 1. As a consequence, the square-shaped vessel 2 loaded in the opening 4 of the holder 9 rotates together with the latter, subjecting the reaction solution, which comprises a mixture of the reagent and the specimen to be examined, to an intense agitation. After the lapse of the time interval determined by the variable resistor R, the timer 16 interrupts the energization of the oscillator 15, whereupon the solenoid 14 ceases to move. At this time, the positioning member 11 will come to a stop abutting the lug 12, so that the openings 9a and 5 are aligned, and the side 2a in which the opening 9a is formed is located on the optical axis of radiation flux P. The photometric process may then take place in the same manner as before, by passing radiation flux P from the source 6 and receiving the radiation by a photoelectric transducer element 7 in order to determine the absorbance of the reaction solution.

In the embodiment described, the square form of the reaction vessel contributes to a more effective agitation by preventing a smooth flow of the reaction solution around the corner. However, it is not essential that the reaction vessel be square in cross section; a vessel of any other cross-sectional configuration, such as a polygon or an ellipse, may be used which can be loaded so as to be immobilized within the holder 9.

By experiments, it is found that when the apparatus is used with a square-shaped, bottomed reaction vessel to mix blood serum to be examined and a reagent in a ratio of 1 to 10, a complete agitation is achieved by energizing the solenoid 14 for a time interval of five seconds to cause an oscillation thereof at a rate of five vertical oscillations and five oscillatory rotations per second.

The use of the joint 13 to connect the shaft 10 with the output shaft 14a of the solenoid 14 has the thermal isolation effect of preventing heat flow between the thermostat block 1 and the solenoid 14.

Both the block 1 and the holder 9 are formed of materials having a good thermal conductivity so that no temperature differential occurs therebetween during the time the holder 9 is subjected to oscillations within the opening 8, thus allowing a satisfactory agitation by simply closing the start switch S.

While the invention has been described as applied to the determination of the absorbance for the purpose of determining the quantity of an enzyme contained in a blood sample, it should be understood that the invention is equally applicable to any kind of liquid agitation apparatus.

Also, the use of the rotary solenoid as means for producing an oscillation which is imparted to the reaction solution may be replaced by any other means which imparts oscillations to the holder in order to agitate the reaction solution in a uniform manner. For example, a reversible motor may be used with the rotational reaction of the motor being periodically, with the motor drive being transmitted to the reaction vessel for agitating the reaction solution contained therein.

What is claimed is:

1. A liquid agitation apparatus for an absorbance measuring apparatus, comprising:
   at least one transparent reaction vessel for containing a reaction solution to be examined;
   a holder for removably containing one said vessel for agitating said reaction solution contained in said one vessel for photometry, said holder being formed with opposing photometric openings for allowing a photometric radiation flux to pass through said reaction solution contained in said one vessel;
   a thermostat block having means for receiving said holder, said thermostat block including means for heating said vessel;
   means for vibrating said holder in order to agitate said reaction solution in said one vessel, said vibrating means being connected to said holder via a resilient joint and said holder further comprising a support shaft connected to said resilient joint; and
   means for positioning said holder so that when said holder is not being vibrated, its photometric openings have a set alignment, said positioning means comprising:
   a positioning member rigidly connected to said support shaft;
   a stationary lug for blocking rotary motion of said positioning member past a set position corresponding to said set alignment of said holder;
   and means for biasing said positioning member against said stationary lug when said holder is not being vibrated.

2. A liquid agitation apparatus according to claim 1, in which said means for vibrating said holder comprises: a rotary solenoid connected with said holder through said resilient joint; an oscillator for applying oscillating electrical signals to said solenoid; and an electronic timer for controlling the operation of said oscillator.

3. A liquid agitation apparatus according to claim 2 in which said oscillator comprises a square wave oscillator.

4. A liquid agitation apparatus according to claim 2 in which said joint comprises a coiled spring.

5. A liquid agitation apparatus according to claim 2, in which said joint comprises a rubber tube.

* * * * *